United States Patent [19]
Bell et al.

[11] Patent Number: 5,856,341
[45] Date of Patent: Jan. 5, 1999

[54] BENZO [B] INDENO [2,1-D] THIOPHENE COMPOUNDS, INTERMEDIATES, PROCESSES, COMPOSITIONS AND METHODS

[75] Inventors: Michael Gregory Bell; Brian Stephen Muehl; Mark Alan Winter, all of Indianapolis, Ind.

[73] Assignee: Eli Lilly and Company, Indianapolis, Ind.

[21] Appl. No.: 933,715

[22] Filed: Sep. 19, 1997

[51] Int. Cl.$^6$ .................... A61K 31/445; C07D 409/12
[52] U.S. Cl. .................... 514/324; 514/212; 514/232.8; 514/422; 514/443; 540/596; 544/145; 546/202; 548/527; 549/42
[58] Field of Search .............. 546/202; 514/212, 514/232.8, 324, 422, 443; 540/596; 544/145; 548/527; 549/42

[56] References Cited

U.S. PATENT DOCUMENTS

| | | | |
|---|---|---|---|
| 3,274,213 | 9/1966 | Lednicer et al. | 546/205 |
| 3,394,125 | 7/1968 | Crenshaw | 548/525 |
| 3,413,305 | 11/1968 | Crenshaw | 548/525 |
| 4,133,814 | 1/1979 | Jones et al. | 260/326 |
| 4,230,862 | 10/1980 | Suarez et al. | 546/237 |
| 4,358,593 | 11/1982 | Jones et al. | 546/202 |
| 4,380,635 | 4/1983 | Peters | 546/202 |
| 4,418,068 | 11/1983 | Jones et al. | 546/237 |
| 5,147,880 | 9/1992 | Jones et al. | 514/650 |
| 5,395,842 | 3/1995 | Labrie | 514/320 |
| 5,470,854 | 11/1995 | Angerer et al. | 514/233 |
| 5,472,962 | 12/1995 | Koizumi et al. | 514/324 |
| 5,484,795 | 1/1996 | Bryant et al. | 514/212 |

FOREIGN PATENT DOCUMENTS

| | | |
|---|---|---|
| 062 503 | 10/1982 | European Pat. Off. |
| WO 89/0289 | 4/1989 | WIPO |
| WO 95/10513 | 4/1995 | WIPO |

OTHER PUBLICATIONS

Sauter et al. "Chemistry of sulfur–containing heterocycles. IV . . . " CA 71:61107, 1969.
Crenshaw, R.R., et al, *J. Med. Chem.* 14(12):1185–1190 (1971).
Jones, C.D., et al, *J. Med. Chem.* 27: 1057–1066) 1984.
Jones, C.D., et al, *J. Med. Chem.* 35: 931–938 1992.

*Primary Examiner*—Ceila Chang
*Attorney, Agent, or Firm*—Janelle D. Strode; David E. Boone

[57] ABSTRACT

The invention provides benzo[b]indenothiophene compounds of formula I

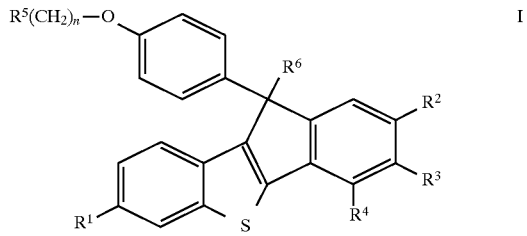

wherein, $R^1$, $R^2$, $R^3$, $R^4$, $R^5$, and $R^6$, are as defined in the specification, intermediates, formulations, and methods of inhibiting bone loss or bone resorption, particularly osteoporosis, cardiovascular-related pathological conditions including hyperlipidemia and related cardiovascular pathologies, and estrogen-dependent cancer.

16 Claims, No Drawings

BENZO [B] INDENO [2,1-D] THIOPHENE COMPOUNDS, INTERMEDIATES, PROCESSES, COMPOSITIONS AND METHODS

BACKGROUND OF THE INVENTION

This application claims the benefit of U.S. Provisional application Ser. No. 60/026,749 filed Sep. 26, 1996.

Osteoporosis describes a group of diseases which arises from diverse etiologies, but which are characterized by the net loss of bone mass per unit volume. The consequence of this loss of bone mass and resulting bone fracture is the failure of the skeleton to provide adequate support for the body. One of the most common types of osteoporosis is associated with menopause. Most women lose from about 20% to about 60% of the bone mass in the trabecular compartment of the bone within 3 to 6 years after the cessation of menses. This rapid loss is generally associated with an increase of bone resorption and formation. However, the resorptive cycle is more dominant and the result is a net loss of bone mass. Osteoporosis is a common and serious disease among postmenopausal women.

There are an estimated 25 million women in the United States alone who are afflicted with this disease. The results of osteoporosis are personally harmful, and also account for a large economic loss due to its chronicity and the need for extensive and long term support (hospitalization and nursing home care) from the disease sequelae. This is especially true in more elderly patients. Additionally, although osteoporosis is generally not thought of as a life threatening condition, a 20% to 30% mortality rate is related to hip fractures in elderly women. A large percentage of this mortality rate can be directly associated with postmenopausal osteoporosis.

The most vulnerable tissue in the bone to the effects of postmenopausal osteoporosis is the trabecular bone. This tissue is often referred to as spongy or cancellous bone and is particularly concentrated near the ends of the bone (near the joints) and in the vertebrae of the spine. The trabecular tissue is characterized by small osteoid structures which interconnect with each other, as well as the more solid and dense cortical tissue which makes up the outer surface and central shaft of the bone. This interconnected network of trabeculae gives lateral support to the outer cortical structure and is critical to the biomechanical strength of the overall structure. In postmenopausal osteoporosis, it is primarily the net resorption and loss of the trabeculae which leads to the failure and fracture of bone. In light of the loss of the trabeculae in the postmenopausal woman, it is not surprising that the most common fractures are those associated with bones which are highly dependent on trabecular support, for example, the vertebrae, the neck of the weight-bearing bones such as the femur and the forearm. Indeed, hip fracture, collies fractures, and vertebral crush fractures are hallmarks of postmenopausal osteoporosis.

The most generally accepted method for the treatment of postmenopausal osteoporosis is estrogen replacement therapy. Although therapy is generally successful, patient compliance with the therapy is low, primarily because estrogen treatment frequently produces undesirable side effects. An additional method of treatment would be the administration of a bisphosphonate compound, such as, for example, Fosamax® (Merck & Co., Inc.).

Throughout premenopausal time, most women have less incidence of cardiovascular disease than men of the same age. Following menopause, however, the rate of cardiovascular disease in women slowly increases to match the rate seen in men. This loss of protection has been linked to the loss of estrogen and, in particular, to the loss of estrogen's ability to regulate the levels of serum lipids. The nature of estrogen's ability to regulate serum lipids is not well understood, but evidence to date indicates that estrogen can up regulate the low density lipid (LDL) receptors in the liver to remove excess cholesterol. Additionally, estrogen appears to have some effect on the biosynthesis of cholesterol, and other beneficial effects on cardiovascular health.

It has been reported in the literature that serum lipid levels in postmenopausal women having estrogen replacement therapy return to concentrations found in the premenopausal state. Thus, estrogen would appear to be a reasonable treatment for this condition. However, the side effects of estrogen replacement therapy are not acceptable to many women, thus limiting the use of this therapy. An ideal therapy for this condition would be an agent which regulates serum lipid levels in a manner analogous to estrogen, but which is devoid of the side effects and risks associated with estrogen therapy.

Estrogen dependent cancers are major diseases effecting both women and to a lesser extent men. Cancer cells of this type are dependent on a source of estrogen to maintain the orginal tumor as well as to proliferate and metasize to other locations. The most common forms of estrogen dependent cancer are breast and uterine carcinomas. Current chemeotherapy of these diseases relies primarily on the use of anti-estrogens, predominately tamoxifene. The use of Tamoxifene, although efficaceous, is not without undesirable side-effects, for example, estrogen agonist properties, such as uterine hypertrophy and carcinogenic potential. Compounds of the current invention while showing the same or better potential for anti-cancer activity, also demonstrate a lower potential for estrogen agonist activity.

In response to the clear need for new pharmaceutical agents which are capable of alleviating the symptoms of, inter alia, postmenopausal syndrome, the instant invention provides benzo[b]indeno[2,1-d]thiophene compounds, pharmaceutical formulations thereof, and methods of using such compounds for the treatment of postmenopausal syndrome and other estrogen-related pathological conditions.

SUMMARY OF THE INVENTION

The instant invention relates to compounds of formula I:

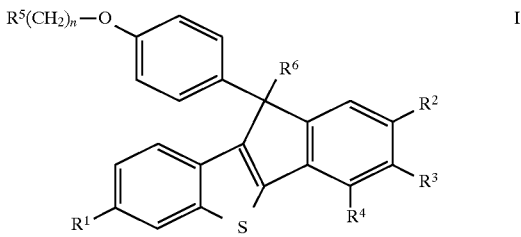

wherein:
$R^1$ is —H, —OH, —X, where —X is a halogen, —O($C_1$-$C_4$ alkyl), —OCO($C_1$-$C_6$ alkyl), —OCO(O) ($C_1$-$C_6$ alkyl), —OCOAr, —OCO(O)Ar where Ar is phenyl or substituted phenyl, or —OSO$_2$($C_4$-$C_6$ alkyl);
$R^2$, $R^3$, and $R^4$ are independently —H, —OH, —X, where —X is a halogen, —O($C_1$-$C_4$ alkyl), —OCO($C_1$-$C_6$ alkyl), —OCO(O)($C_1$-$C_6$ alkyl), —OCOAr, —OCO (O)Ar where Ar is phenyl or substituted phenyl, or —OSO$_2$($C_4$-$C_6$ alkyl);
n is 2 or 3;
$R^5$ is 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino; and R$^6$ is —H, —OH, —X, where —X is a halogen, —CN, —NH$_2$, —NHR$^8$, —NR$^8$R$^9$, where R$^8$ and R$^9$ are both independently C$_1$–C$_6$ alkyl, or C$_1$–C$_6$ alkyl;

or a pharmaceutically acceptable salt or solvate thereof.

The instant invention also relates to compounds of formula XIII which are useful as intermediates for the synthesis of compounds of formula I:

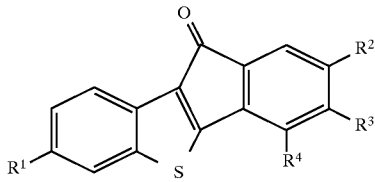

XIII wherein:

R$^1$, R$^2$, R$^3$, and R$^4$ are as previously defined, with the proviso that R$^1$, R$^2$, R$^3$, and R$^4$ are not all hydrogen.

The instant invention further provides pharmaceutical formulations containing compounds of formula I, and the use of said compounds and/or formulations at least for the inhibition of bone loss or bone resorption, particularly osteoporosis, cardiovascular-related pathological conditions including hyperlipidemia, and estrogen-dependent cancer.

DETAILED DESCRIPTION OF THE INVENTION

General terms used in the description of compounds herein described bear their usual meanings. For example, "C$_1$–C$_6$ alkyl" refers to straight or branched aliphatic chains of 1 to 6 carbon atoms including methyl, ethyl, propyl, isopropyl, butyl, n-butyl, pentyl, isopentyl, hexyl, isohexyl, and the like. Similarly, the term "—OC$_1$–C$_4$ alkyl" represents a C$_1$–C$_4$ alkyl group attached through an oxygen such as, for example, methoxy, ethoxy, n-propoxy, isopropoxy, and the like. Of these C$_1$–C$_4$ alkoxy groups, methoxy is highly preferred.

The term "substituted phenyl" refers to a phenyl group having one or more substituents selected from the group consisting of C$_1$–C$_4$ alkyl, —OC$_1$–C$_4$ alkyl, hydroxy, nitro, chloro, fluoro, or tri(chloro or fluoro)methyl, and the like.

The term "hydroxy protecting group" contemplates numerous functionalities used in the literature to protect a hydroxy function during a chemical sequence, and which can be removed to yield the phenol. Included within this group would be acyls, mesylates, tosylates, benzyl, alkylsilyloxys, —OC$_1$–C$_4$ alkyls, and the like. Numerous reactions for the formation and removal of such protecting groups are described in a number of standard works including, for example, *Protective Groups in Organic Chemistry*, Plenum Press (London and New York, 1973); Green, T. W., Protective Groups in Organic Synthesis, Wiley, (New York, 1981); and *The Peptides*, Vol. I, Schrooder and Lubke, Academic Press (London and New York, 1965). Methods for removing preferred hydroxy protecting groups, particularly methyl, are essentially as described in the Examples infra.

The term "inhibit" includes its generally accepted meaning which includes prohibiting, preventing, restraining, and slowing, stopping, or reversing progression, severity, or ameliorating a resultant symptom or effect.

The term "solvate" represents an aggregate that comprises one or more molecules of the solute, such as a formula I compound, with one or more molecules of solvent.

Compounds of formula I would include:

10-[4-[2-(1-Piperidinyl)ethoxy]phenyl]-3,7-dimethoxy benzo[b]indeno[2,1-d]thiophene;

10-[4-[2-(1-Piperidinyl)ethoxy]phenyl]benzo[b] indeno[2,1-d] thiophene;

10-[4-[2-(1-Piperidinyl)ethoxy]phenyl]-3,7-dihydroxy benzo[b]indeno[2,1-d]thiophene;

10-[4-[2-(1-Piperidinyl)ethoxy]phenyl]-7-methoxy benzo [b]indeno[2,1-d]thiophen-10-ol;

10-[4-[2-(1-Piperidinyl)ethoxy]phenyl]-2,7-dimethoxy benzo[b]indeno[2,1-d]thiophen-10-ol;

10-[4-[2-(1-Piperidinyl)ethoxy]phenyl]-7-hydroxy benzo[b] indeno[2,1-d]thiophen-10-ol;

10-[4-[2-(1-Piperidinyl)ethoxy]phenyl]-7-methoxy benzo [b]indeno[2,1-d]thiophene;

10-[4-[2-(1-Piperidinyl)ethoxy]phenyl]-2,7-dimethoxybenzo[b]indeno[2,1-d]thiophene;

10-[4-[2-(1-Piperidinyl)ethoxy]phenyl]-7-hydroxy benzo[b] indeno[2,1-d]thiophene hydrochloride, 10-[4-[2-(1-Pyrrolidinyl)ethoxy]phenyl]-3,7-dimethoxy benzo[b]indeno[2,1-d]thiophene;

10-[4-[2-(1-Pyrrolidinyl)ethoxy]phenyl]benzo[b]indeno[2,1-d] thiophene;

10-[4-[2-(1-Pyrrolidinyl)ethoxy]phenyl]-3,7-dihydroxy benzo[b]indeno[2,1-d]thiophene;

10-[4-[2-(1-Pyrrolidinyl)ethoxy]phenyl]-7-methoxy benzo [b]indeno[2,1-d]thiophen-10-ol;

10-[4-[2-(1-Pyrrolidinyl)ethoxy]phenyl]-2,7-dimethoxy benzo[b]indeno[2,1-d]thiophen-10-ol;

10-[4-[2-(1-Pyrrolidinyl)ethoxy]phenyl]-7-hydroxy benzo [b]indeno[2,1-d]thiophen-10-ol;

10-[4-[2-(1-Pyrrolidinyl)ethoxy]phenyl]-7-methoxy benzo [b]indeno[2,1-d]thiophene;

10-[4-[2-(1-Pyrrolidinyl)ethoxy]phenyl]-2,7-dimethoxybenzo[b]indeno[2,1-d]thiophene;

10-[4-[2-(1-Pyrrolidinyl)ethoxy]phenyl]-7-hydroxy benzo [b]indeno[2,1-d]thiophene hydrochloride, and the like.

The term "leaving group" means a chemical entity which is capable of being displaced by an amino function via an SN$_2$ reaction. Such reactions are well known in the art and such groups would include halogens, mesylates, tosylates, and the like. A preferred leaving group is bromo.

The compounds of formula I are derivatives of benzo[b] indenothiophene, which is named and numbered according to the Ring Index, The American Chemical Society, as follows:

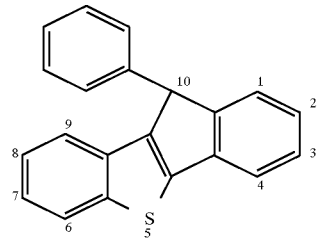

Several synthetic pathways are available for preparing intermediates employed in the instant invention. One synthetic route is illustrated in Schemes I and II, below. This overall route is similar to that described in U.S. Pat. No. 5,420,349, the disclosure of which is herein incorporated by reference.

The starting material for the preparation of the intermediates here is a 2-aminobenzothiophene of formula III. Its preparation and structure are provided in Scheme I below.

Scheme I

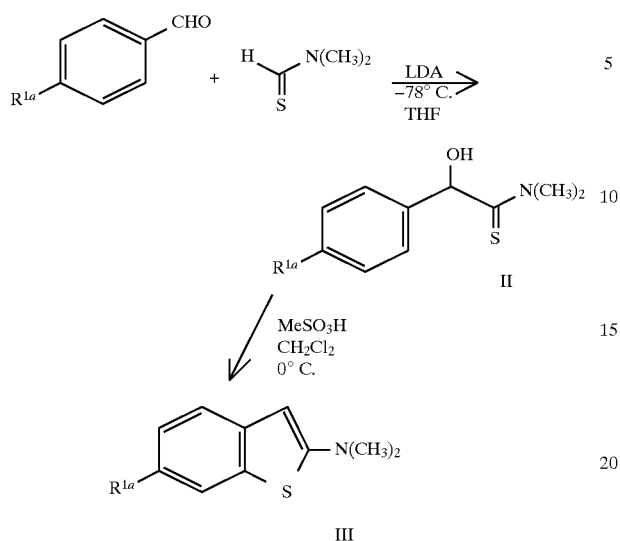

wherein $R^{1a}$ is —H or —$OR^7$, where $R^7$ is a hydroxy protecting group.

The synthesis of compound III, wherein $R^1$ is methoxy, is also described in Ablenas, et al., *Can. J. Chem.*, 65, 1800–1803 (1987), the disclosure of which is herein incorporated by reference.

Scheme II

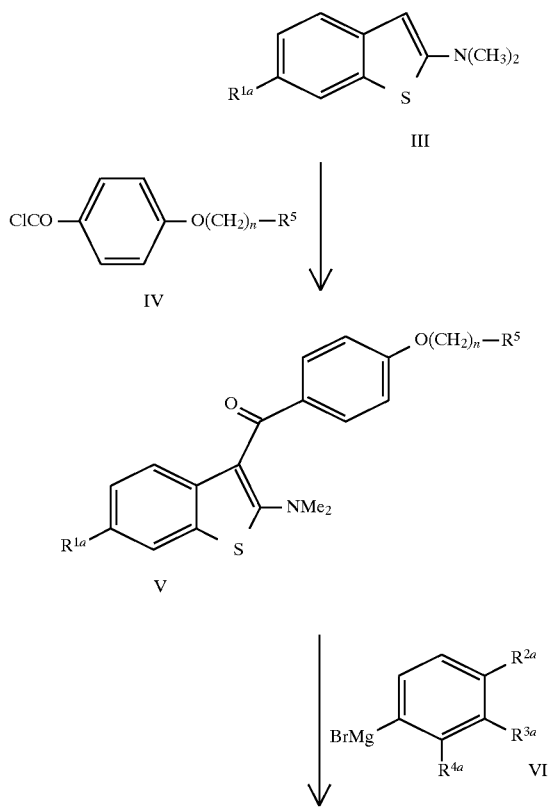

-continued
Scheme II

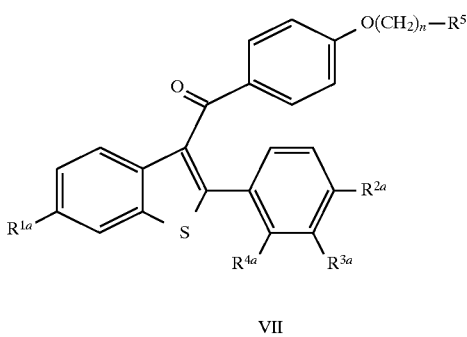

wherein:

$R^{1a}$, $R^5$, and n are as previously defined, and
$R^{2a}$, $R^{3a}$, and $R^{4a}$ are —H, —$OR^7$, where $R^7$ is a hydroxy protecting group, —F, —Cl, and $C_1$–$C_4$ alkyl.

The compounds of formula III are coupled with an acid chloride of formula IV to form the intermediate keto-benzo[b]thiophene, V. This coupling reaction is a standard Friedel-Crafts acylation and is catalyzed by either a Lewis acid or a proton acid. A preferred Lewis acid is $AlCl_3$. This reaction may be carried out in a variety of inert solvents, such as halogenated hydrocarbons, ethers, and the like. This reaction may be run at a variety of temperatures, usually, between 25°–150° C. and the reaction is complete within one to twenty hours, depending on the exact conditions (Olah, G., "Friedel-Crafts and Related Reactions", Interscience Publications, New York, London, and Sidney, 1963, Vol. I, Ch. III and IV). Preferred conditions for the current invention utilize chlorobenzene as a solvent, and a reaction temperature of 100°–105° C. The reaction is completed in about nine hours. The compounds of formula IV may be prepared via the methods described in Jones et al., *J. Med. Chem.*, 27, 1057 (1984) and U.S. Pat. Nos. 4,133,814, 4,380,635, and 4,418,068, the disclosures of which are herein incorporated by reference.

Briefly, 4-hydroxybenzoic acid is O-alkylated on the phenolic hydroxyl with a compound, $R^5(CH_2)_nCl$ (Br), in the presence of a strong base, such as, $K_2CO_3$, $CsCO_3$, NaH, and the like. Such reactions are usually run in an inert solvent such as, for example, THF, DMF, ether, and the like, at temperatures between 25°–150° C. The O-alkylated benzoic acid product is converted to its acid chloride by treatment with a chlorinating agent, such as thionyl chloride. Compound IV may be used as its free base or as a salt.

The second synthetic pathway of Scheme II continues with the reaction of V with a Grignard reagent of formula VI. This reaction is a 1,4 addition on the 3-ketone with elimination of the 2-amino. The preferred bromo Grignard reagents may be prepared by reacting the bromo derivatives of a formula VI compound with magnesium at ambient temperature in ether. The bromo precursors of formula VI compounds are either commercially available or can be obtained from methods known in the art. Such compounds of formula VI would include: 1-bromo-2-methoxybenzene, 1-bromo-3-methoxybenzene, 1-bromo-2-ethylbenzene, 1-bromo-3-methylbenzene, 1-bromo-2,4-difluorobenzene, 1-bromo-3-chlorobenzene, 1-bromo-2-chlorobenzene, 1-bromo-2-fluorobenzene, 2-bromo-4-fluoroanisole, 4-bromo-2-fluoroanisole, and the like. The addition reaction may be run at temperatures between 25° and −78° C. in inert solvents, such as THF, ethyl ether, dioxane, and the like. The reaction of V with VI yields compounds of formula VII.

A compound of formula VII is then used in the preparation of a compound of formula I as provided in Scheme III below.

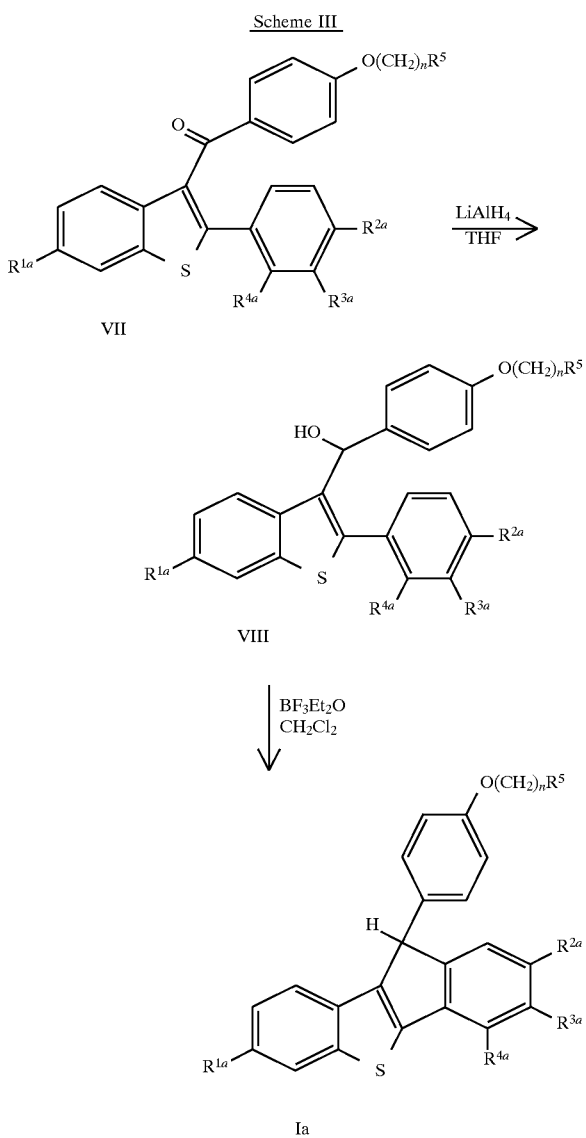

wherein $R^{1a}$, $R^{2a}$, $R^{3a}$, $R^{4a}$, $R^5$, and n are as previously defined.

A compound of formula VII is reduced to form a carbinol of formula VIII, typically by the use of lithium aluminum hydride in a suitable solvent, such as THF.

The formation of the indenobenzothiophene of formula Ia is effected by the ring closure of a compound of formula VIII, which may be performed in the presence of a suitable acid, such as boron trifluoride, and a solvent, such as dichloromethane.

Another route in the synthesis of compounds of formula I employs the route as illustrated by Schemes IV, V, VI, and VII provided hereinbelow.

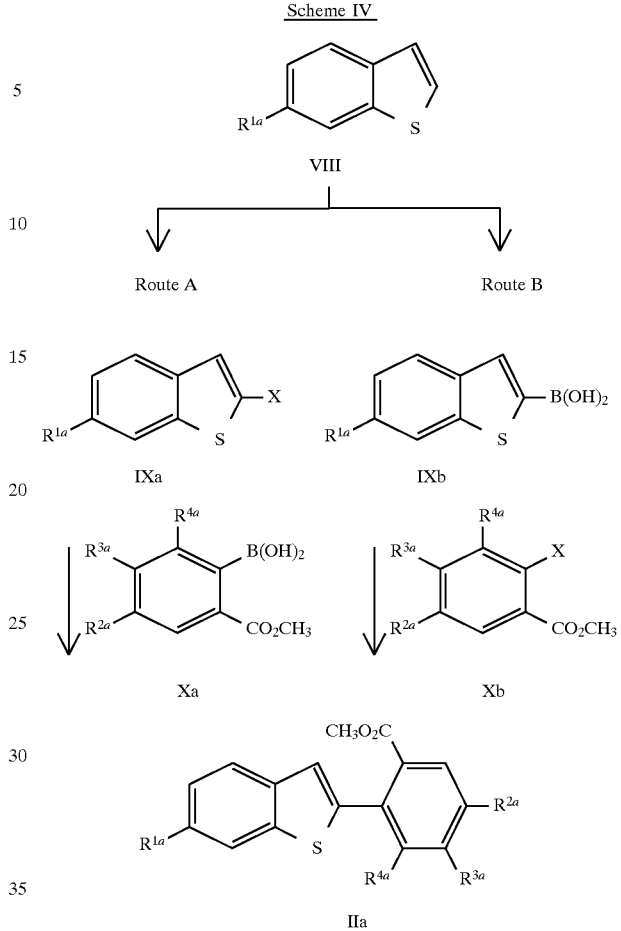

wherein $R^{1a}$, $R^{2a}$, $R^{3a}$, and $R^{4a}$ have their previous meanings; and X is a halogen.

Compounds of formula VIII may be prepared by methods at least as described in Jones et al., supra. Compounds of formula VIII are arylated in the 2-position via Suzuki coupling [see, for example, Suzuki, A., *Pure and Appl. Chem.*, 6(2):213–222 (1994)]. Using one Suzuki coupling option, a formula VIII compound is selectively halogenated at the 2-position (VIIIa), and then coupled with an arylboronic acid compound of formula IXa (Scheme IV, Route A) to provide intermediate compounds of formula XI.

Preferably, however, an arylboronic acid of formula IXb is formed from a compound of formula VIII, and then reacted with a halo-arene of formula Xb to give intermediates of formula XI (Scheme IV, Route B). Such intermediates (XI) are useful for preparing pharmaceutically active compounds of the present invention (compounds of formula I).

The first step in Route A in Scheme IV is the 2-position iodination or bromination of a formula VIII compound using standard procedures. Generally, a formula VIII compound is reacted with a slight excess of n-butyllithium in hexane, in an appropriate solvent and under an inert atmosphere such as nitrogen, followed by the dropwise addition of a slight excess of the desired halogenating agent in an appropriate solvent. Preferably the halogenating agent for this step is iodine. However, the use of bromine, such as, for example, N-bromosuccinimide, is sufficient.

Appropriate solvents include an inert solvent or mixture of solvents such as, for example, diethyl ether, dioxane, and tetrahydrofuran (THF). Of these, tetrahydrofuran, particularly anhydrous THF, is preferred.

The present selective, 2-position halogenation reaction is optionally run at a temperature from about −75° C. to about −85° C.

The product of the above reaction, a halo-arene of formula IXa, is then coupled with an arylboronic acid of formula Xa, via standard Suzuki coupling procedures, to provide compounds of formula XI. Compounds of formula Xa are derived from commercially available compounds via procedures well known to one of ordinary skill in the art (see, for example, March J.; and Suzuki, A., supra).

In the present coupling reaction, a slight excess of a formula Xa compound is reacted with each equivalent of a formula IXa compound in the presence of a palladium catalyst and an appropriate base in an inert solvent, such as toluene.

Although various palladium catalysts drive Suzuki coupling reactions, the catalyst selected is usually reaction-specific. The use of a triphenylphosphine palladium catalyst in the present reaction is a preferred catalyst.

Likewise, various bases may be used in the present coupling reaction. However, it is preferred to use triethylamine. The temperature employed in this step should be sufficient to effect completion of the coupling reaction. Typically, heating the reaction mixture to reflux for a period from about 2 to about 4 hours is adequate.

In Route B of Scheme IV, a 2-position arylboronic acid of formula IXb is prepared using well known procedures. Generally, a compound of formula VIII is treated with a slight excess of n-butyllithium in hexanes, in an appropriate solvent, and under an inert atmosphere, such as nitrogen, following by the dropwise addition of an appropriate trialkylborate.

Appropriate solvents include an inert solvent or mixture of solvents such as, for example, diethyl ether, dioxane, and tetrahydrofuran (THF). THF, particularly anhydrous THF, is preferred. The preferred trialkylborate used in the present reaction is triisopropyl borate.

The product of this reaction, a compound of formula IXb, is then reacted with an aryl halide or aryl triflate of formula Xb, via standard Suzuki coupling procedures, to provide compounds of formula XI. The preferred reaction conditions for the present reaction are as described for the reaction of compounds of formula IXa and Xa, in Scheme IV, which also provide compounds of formula XI.

Compounds of formula XI are then cyclized to provide the indenobenzothiophene intermediates of formula XIIIa, as provided below in Scheme V.

Scheme V

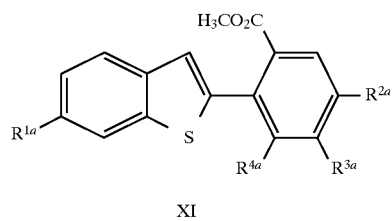

XI

NaOH
THF
EtOH

-continued
Scheme V

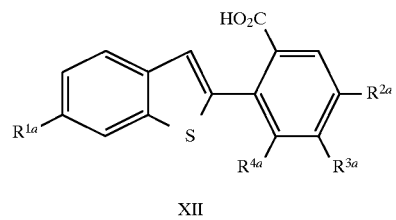

XII

1) SOCl₂
   ClCH₂CH₂Cl
2) AlCl₃
   CH₂Cl₂

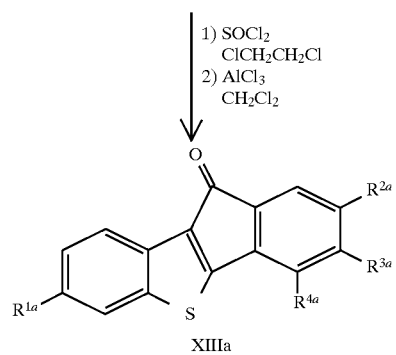

XIIIa

A compound of formula XI is demethylated to provide the carboxylic acid derivative of formula XII, typically in the presence of a strong base.

A compound of formula XII is then cyclized to provide the indenobenzothiophene intermediate of formula XIIIa. This cyclization is effected by Friedel-Crafts acylation, which has been previously described hereinabove.

An additional means of generating the compounds of formula XIIIa is provided in Scheme VI below, wherein a compound of formula XIV is also cyclized using Friedel-Crafts acylation to provide a compound of formula XIIIa.

Scheme VI

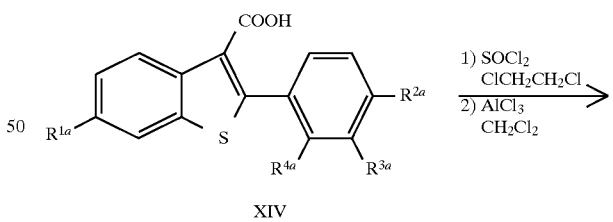

XIV

1) SOCl₂
   ClCH₂CH₂Cl
2) AlCl₃
   CH₂Cl₂

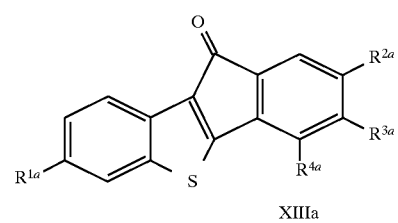

XIIIa

The compounds of formula XIV may be conveniently prepared by the methods provided in Scheme VII, below.

Scheme VII

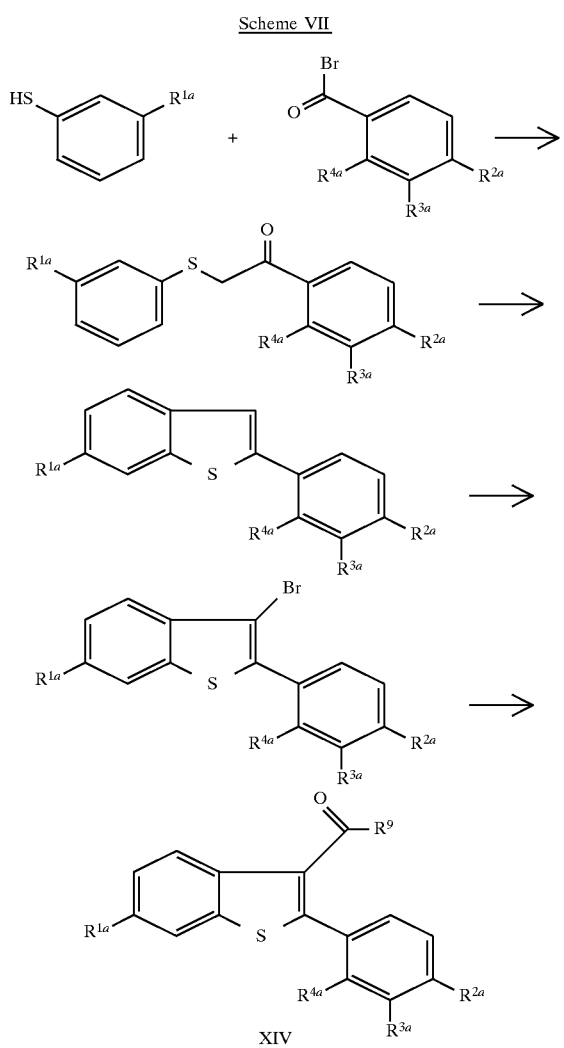

The Formula XIV compounds, wherein $R^{1a}$, $R^{2a}$, $R^{3a}$, and $R^{4a}$ are as defined above, can be prepared by first reacting a 3-alkoxybenzenethiol with a phenacyl or 4'-alkoxyphenacyl bromide in the presence of a strong base.

Suitable bases for this transformation include, potassium hydroxide and sodium hydroxide. The reaction is typically carried out in ethanol or a mixture of water and ethanol at a temperature of about 0° C. to about 50° C.

The next step is cyclization of the arylphenacylsulfide. The cyclization is conveniently carried out by heating the arylphenacylsulfide in polyphosphoric acid. The cyclization is typically carried out at a temperature of about 80° C. to about 120° C., preferably between 85° C. and 90° C. The intermediate benzothiophene is typically purified by recrystallization. For example, when $R^{1a}$ and $R^{2a}$ are methoxy, the intermediate benzothiophene compound may be recrystallized from ethyl acetate.

The intermediate benzothiophene compound is converted to a Formula XIV compound by a sequence of steps comprising halogenation, lithiation, and carboxylation. First, the benzothiophene intermediate is converted to the corresponding 3-bromo analog by reaction with bromine in a halogenated hydrocarbon solvent. Suitable halogenated solvents for this reaction include carbon tetrachloride, chloroform, and methylene chloride; preferably a mixture of carbon tetrachloride and chloroform. This transformation is carried out at a temperature of about 25° C. to about 55° C. The intermediate 3-bromo benzothiophene compound is isolated using standard techniques, such as by recrystallization.

The 3-bromo intermediate is lithiated and carboxylated to prepare the Formula XIV compound. The 3-bromo benzothiophene compound is reacted with an alkyl lithium, such as n-butyl lithium in a dry, polar organic solvent to produce the lithiated compound. Suitable solvents for this reaction include anhydrous diethyl ether, anhydrous tetrahydrofuran, and anhydrous dimethoxyethane. This reaction is typically run at the temperature of about –78° C. to about –50° C. The intermediate 3-lithiated benzothiophene compound is treated with carbon dioxide, either solid or gaseous, to produce the Formula XIV compound wherein $R^9$ is —OH. This transformation is conveniently carried out in the same solvent as the lithiation reaction. The acid is typically isolated by acidification of the reaction mixture followed by recrystallization. For example, when $R^{1a}$ and $R^{2a}$ are methoxy and $R^9$ is hydroxy, the Formula XIV compound can be recrystalized from absolute ethanol.

The benzo[b]indenothiophene intermediates of formula XIIIa are then employed in the further synthesis of the compounds of formula I. This is illustrated in Scheme VIII below.

Scheme VIII

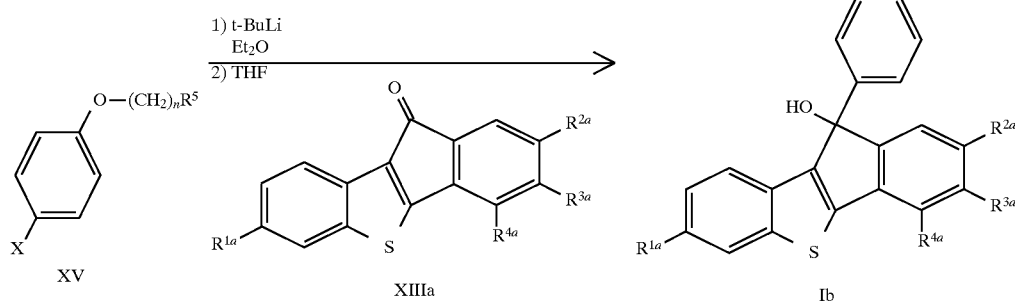

-continued
Scheme VIII

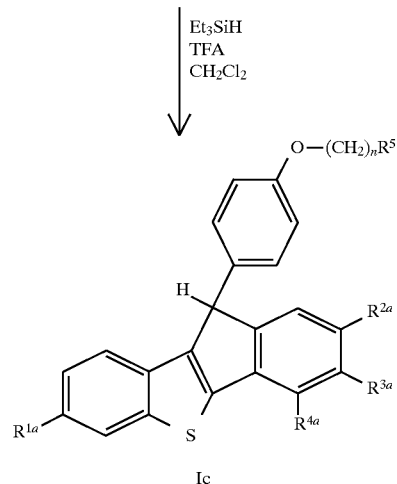

The aryl halide of formula XV is coupled with the indenobenzothiophene of formula XIIIa to generate a compound of formula Ib. A compound of formula Ib may then be reduced to provide a compound of formula Ic. Deprotection of a compound of formula Ic results in a compound of formula Id, one example of which is provided below in Scheme IX.

Scheme IX

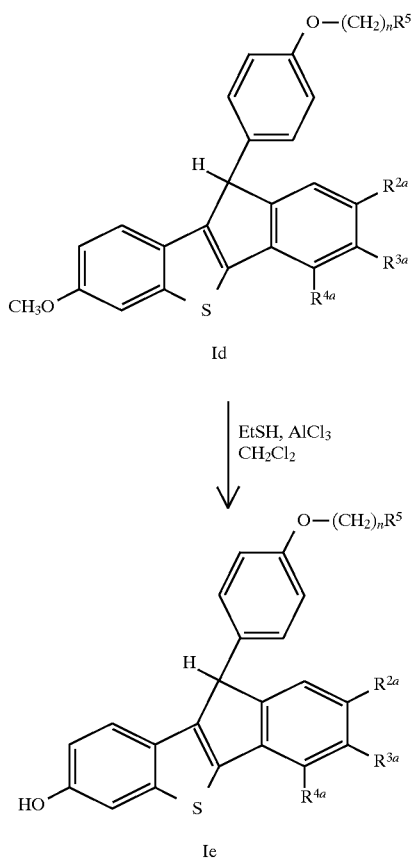

Compounds of formula Ia, Ib, Ic, Id, and Ie are pharmaceutically active for the methods described herein, and are encompassed by formula I. Both isomers and mixtures of isomers generated at the 10-position are contemplated by, and within the scope of, the compounds of formula I.

Although the free-base form of formula I compounds can be used in the methods of the instant invention, it is preferred to prepare and use a pharmaceutically acceptable salt form. The term "pharmaceutically acceptable salt" refers to either acid or base addition salts which are known to be non-toxic and are commonly used in the pharmaceutical literature. The pharmaceutically acceptable salts generally have enhanced solubility characteristics compared to the compound from which they are derived, and thus are often more amenable to formulation as liquids or emulsions. The compounds used in the methods of this invention primarily form pharmaceutically acceptable acid addition salts with a wide variety of organic and inorganic acids, and include the physiologically acceptable salts which are often used in pharmaceutical chemistry. Such salts are also part of this invention.

Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl-substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caproate, caprylate, chloride, cinnamate, citrate, formate, fumarate, glycolate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or ethyl acetate. The salt normally precipitates out of solution within about one hour to 10 days and can be isolated by filtration, or the solvent can be stripped off by conventional means. The instant invention further provides for pharmaceutically acceptable formulations for administering to a mammal, including humans, in need of treatment, which comprises an effective amount of a compound of formula I and a pharmaceutically acceptable diluent or carrier.

As used herein, the term "effective amount" means an amount of compound of the instant invention which is capable of inhibiting, alleviating, ameliorating, treating, or preventing further symptoms in mammals, including humans, suffering from bone loss or bone resorption, particularly osteoporosis, and cardiovascular-related pathological conditions including hyperlipidemia and related cardiovascular pathologies.

In the case of estrogen-dependent cancers, the term "effective amount" means the amount of compound of the instant invention which is capable of alleviating, ameliorating, inhibiting cancer growth, treating, or preventing the cancer and/or its symptoms in mammals, including humans.

By "pharmaceutically acceptable formulation" it is meant that the carrier, diluent, excipients and salt must be compatible with the active ingredient (a compound of formula I) of the formulation, and not be deleterious to the recipient thereof. Pharmaceutical formulations can be prepared by procedures known in the art. For example, the compounds of this invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agar agar, calcium carbonate, and sodium bicarbonate; agents for retarding dissollution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate and solid polyethylene glycols. Final pharmaceutical forms may be: pills, tablets, powders, lozenges, syrups, aerosols, saches, cachets, elixirs, suspensions, emulsions, ointments, suppositories, sterile injectable solutions, or sterile packaged powders, and the like, depending on the type of excipient used.

Additionally, the compounds of this invention are well suited to formulation as sustained release dosage forms. The formulations can also be so constituted that they release the active ingredient only or preferably in a particular part of the intestinal tract, possibly over a period of time. Such formulations would involve coatings, envelopes, or protective matrices which may be made from polymeric substances or waxes.

The particular dosage of a compound of formula I required to treat, inhibit, or prevent the symptoms and/ or disease of a mammal, including humans, suffering from the above maladies according to this invention will depend upon the particular disease, symptoms, and severity. Dosage, routes of administration, and frequency of dosing is best decided by the attending physician. Generally, accepted and effective doses will be from 15 mg to 1000 mg, and more typically from 15 mg to 80 mg, one to three times per day. Such dosages will be administered to a patient in need thereof for at least thirty days, and more typically for six months, or chronically.

The formulations which follow are given for purposes of illustration and are not intended to be limiting in any way. The total active ingredients in such formulations comprises from 0.1% to 99.9% by weight of the formulation. The term "active ingredient" means a compound of formula I.

| Formulation 1: Gelatin capsules | |
|---|---|
| Ingredient | Quantity (mg/capsule) |
| Active Ingredient | 0.1–1000 |
| Starch NF | 0–500 |
| Starch flowable powder | 0–500 |
| Silicone fluid 350 centistokes | 0–15 |

The ingredients are blended, passed through a No. 45 mesh U.S. sieve, and filled into hard gelatin capsules.

| Formulation 2: Tablets | |
|---|---|
| Ingredient | Quantity (mg/tablet) |
| Active Ingredient | 2.5–1000 |
| Starch | 10–50 |
| Cellulose, microcrystalline | 10–20 |
| Polyvinylpyrrolidone (as 10% solution in water) | 5 |
| Sodium carboxymethylcellulose | 5 |
| Magnesium stearate | 1 |
| Talc | 1–5 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules thus produced are dried at 50°–60° C. and passed through a No. 18 mesh U.S. sieve. The sodium carboxymethylcellulose, magnesium stearate, and talc, previously passed through a No. 60 mesh U.S. sieve, are added to the above granules and thoroughly mixed. The resultant material is compressed in a tablet forming machine to yield the tablets.

| Formulation 3: Aerosol | |
|---|---|
| Ingredient | Weight % |
| Active Ingredient | 0.25 |
| Ethanol | 29.75 |
| Propellant 22 (Chlorodifluoromethane) | 70.00 |
| Total | 100.00 |

The active ingredient is mixed with ethanol and the mixture added to a portion of the propellant 22, cooled to 30° C. and transferred to a filling device. The required amount is then fed to a stainless steel container and diluted with the remainder of the propellant. The valve units are then fitted to the container.

| Formulation 4: Suppositories | |
|---|---|
| Ingredient | Weight |
| Active ingredient | 150 mg |
| Saturated fatty acid glycerides | 3000 mg |

The active ingredient is passed through a No. 60 mesh U.S. sieve and suspended in the fatty acid glycerides which had previously heated to their melting point. The mixture is poured into a suppository mold and allowed to cool.

Formulation 5: Suspension

Suspensions each containing 0.1–1000 mg of a compound of formula I per 5 mL dose.

| Ingredient | Weight |
|---|---|
| Active Ingredient | 0.1–1000 mg |
| Sodium carboxymethyl cellulose | 50 mg |
| Syrup | 1.25 mL |
| Benzoic acid solution (0.1M) | 0.10 mL |
| Flavor | q.v. |
| Color | q.v. |
| Purified water to total | Total 5 mL |

A compound of formula I is passed through a No. 45 mesh U.S. sieve and mixed with the sodium carboxymethyl cellulose and syrup to form a smooth paste. The benzoic acid solution, flavor, and color diluted in water are added and mixture stirred thoroughly. Additional water is added to bring the formulation to final volume.

The following Examples and Preparations are provided to better elucidate the practice of the instant invention and should not be interpreted in any way as to limit the scope of same. Those skilled in the art will recognize that various modifications may be made while not departing from the spirit and scope of the invention. All publications and patent applications mentioned in the specification are indicative of the level of those skilled in the art to which this invention pertains.

NMR data for the following Examples were generated on a GE 300 MHz NMR instrument, and anhydrous $CDCl_3$ was used as the solvent unless otherwise indicated. Field strength for $^{13}C$ NMR spectra was 75.5 MHz, unless otherwise indicated.

EXAMPLES

Preparation 1

1A. [6-Methoxy-2-(3-methoxyphenyl)benzo[b]thiophen-3-yl][4-[2-(1-piperidinyl)ethoxy]phenyl]methanol

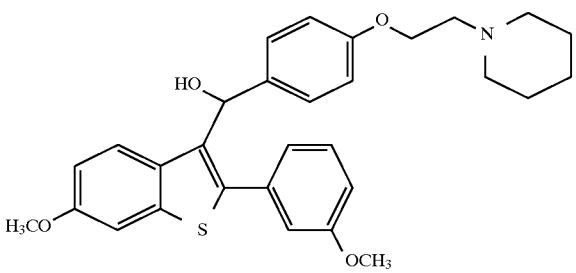

To a solution of 0.21 g of [6-methoxy-2-(3-methoxyphenyl)-benzo[b]thiophen-3-yl][4-[2-(1-piperidinyl)ethoxy]phenyl]methanone in 20 ml THF at 22° C. was slowly added 0.23 g of lithium aluminum hydride. After stirring for 2 hours, the reaction was decomposed by dropwise addition of 0.23 ml water, 0.23 ml 5N NaOH and 0.69 ml water. The resulting mixture was filtered and the granular precipitate washed with 20 ml THF. Evaporation of the combined filtrate and washings provided 0.20 g of the title compound: MS m/z 503 (M+); 300-MHz $^1H$ NMR ($CDCl_3$) δ 1.65 (m.6H), 2.55 (m, 4H), 2.80 (m, 2H), 3.78 (s, 3H), 3.85 (s, 3H), 4.12 (m, 2H), 6.22 (m, 1H), 6.85–7.09 (m, 6H), 7.32 (m, 4H), 7.63 (d, 1H).

1B. [2-Phenylbenzo[b]thiophen-3-yl] [4-[2-(1-piperidinyl)ethoxy]phenyl]methanol

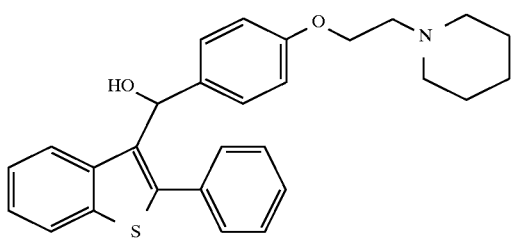

By following the procedure of part A, and substituting [6-methoxy-2-(3-methoxy phenyl)-benzo[b]thiophen-3-yl][4-[2-(1-piperidinyl)ethoxy]phenyl]methanone with [2-phenylbenzo-[b]thiophen-3-yl] [4-[2-(1-piperidinyl)ethoxy]phenyl]methanone; the title compound was obtained: MS m/z 443 (M+); 300-MHz $^1H$ NMR ($CDCl_3$) δ 1.63 (m, 6H), 2.58 (m, 4H), 2.80 (t, 2H), 4.10 (t, 2H), 6.23 (s, 1H), 6.85 (d, J=9 Hz, 2H), 7.19–7.55 (m, 8H), 7.75 (d, J=9 Hz, 1H), 7.84 (d, J=8 Hz, 1H).

Example 1

1A. 10-[4-[2-(1-Piperidinyl)ethoxy]phenyl]-3,7-dimethoxybenzo[b]indeno[2,1-d]thiophene

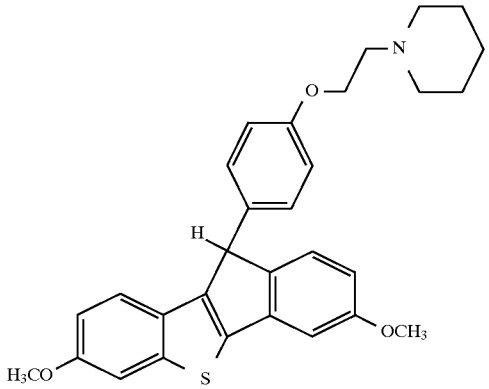

To a solution of 0.21 g of [6-methoxy-2-(3-methoxyphenyl)-benzo[b]thiophen-3-yl] [4-[2-(1-piperidinyl)ethoxy]phenyl]methanol in 20 ml of dichloroethane at 22° C. was added 0.16 ml of trifluoroacetic acid dropwise. After heating at reflux for 2 hours, the reaction solution was cooled to room temperature and quenched by addition of saturated sodium bicarbonate. The organic portion was separated from the mixture and washed with water and brine, dried over sodium sulfate and evaporated to dryness. The resulting oil was chromatographed over silica gel eluting with 2% methanol in chloroform. The desired product was subsequently purified by crystallization from methanol to provide 0.08 g of the title compound as a white crystalline solid: mp 170°–173° C.; MS m/z 485 (M$^+$); Anal. calcd for $C_{30}H_{31}NO_3S$: C, 74.20; H, 6.43; N, 2.88. Found: C, 73.90; H, 6.39; N, 2.71.

1B. 10-[4-[2-(1-Piperidinyl)ethoxy]phenyl]benzo[b] indeno[2,1-d]thiophene

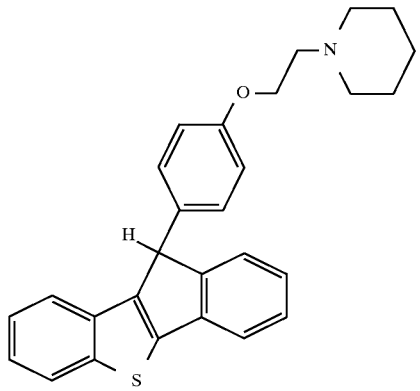

By following the procedure of part A, and substituting [6-methoxy-2-(3-methoxyphenyl)-benzo[b]thiophen-3-yl] [4-[2-(1-piperidinyl)ethoxy]phenyl]methanol with [2-phenylbenzo[b] thiophen-3-yl][4-[2-(1-piperidinyl)ethoxy]phenyl]methanol; the title compound was obtained: MS m/z 425 (M$^+$). Anal. Calcd for $C_{28}H_{27}NOS$: C, 79.02; H, 6.40; N, 3.29. Found: C, 79.31; H, 6.63; N, 3.52.

Example 2

10-[4-[2-(1-Piperidinyl)ethoxy]phenyl]-3,7-dihydroxy benzo[b]indeno[2,1-d]thiophene

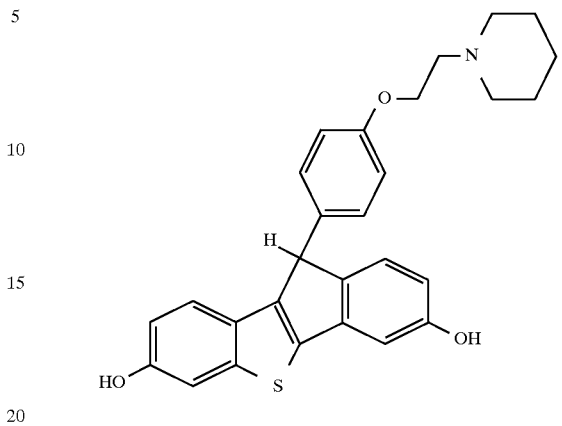

To a solution of 0.51 g of 10-[4-[2-(1-piperidinyl)ethoxy] phenyl]-3,7-dimethoxy-benzo[b]indeno[2,1-d]thiophene in 50 ml methylene chloride at 0° C. was added 0.30 ml of boron tribromide dropwise. The resulting mixture was stirred for 2.5 hours and then quenched with methanol and water. The organic portion was separated from the mixture and the aqueous portion extracted with ethyl acetate. The combined organic extracts were dried (sodium sulfate), filtered, and evaporated. The resulting oil was chromatographed over florisil eluting with 10% methanol in chloroform to give 0.25 g of the title compound as an amorphous solid: MS m/z 458 (M$^+$); Anal. Calcd for $C_{28}H_{27}NO_3S$: C, 73.49; H, 5.95; N, 3.06. Found: C, 73.23; H, 5.93; N, 2.93.

Preparation 2

6-Methoxy-2-[4-methoxy-2-methylbenzoate]benzo[b]thiophene

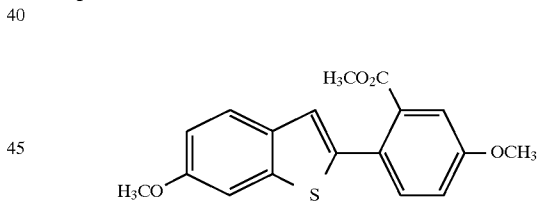

A mixture of 0.50 g of 6-methoxy-benzo[b]thiophen-2-yl boronic acid, 0.60 g of 5-methoxy-2-bromo-methyl benzoate, 0.017 g of palladium (II) acetate, 0.046 g of triphenylphosphine, and 0.87 ml of triethylamine in 25 ml dimethylformamide was heated at 100° C. for 18 hours. The reaction mixture was cooled to room temperature and evaporated. The resulting residue was dissolved in chloroform and water. The organic portion was separated from the mixture and the aqueous portion extracted with chloroform. The combined organic extracts were washed with saturated sodium bicarbonate and brine, dried (sodium sulfate), filtered, and evaporated. The resulting residue was chromatographed over silica gel eluting with 25% hexanes in toluene to provide 0.38 g of the title compound: MS m/z 329 (M$^+$+1); Anal. calcd for $C_{18}H_{16}O_4S$: C, 65.84; H, 4.91. Found: C, 65.84; H, 4.94.

Preparation 3
6-Methoxy-2-[4-methoxy-2-benzoic acid]benzo[b]thiophene

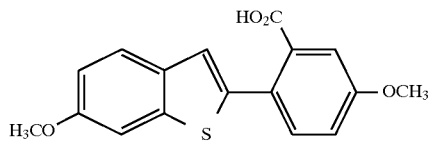

To a solution of 0.11 g of 6-methoxy-2-[4-methoxy-2-methylbenzoate]benzo[b]thiophene in 5 ml of tetrahydrofuran and 3 ml of ethanol at 22° C. was added 1.63 ml of 1N NaOH. The reaction mixture was stirred 18 hours at 22° C. and then heated at 50° C. for 5 hours. After cooling to room temperature, the reaction mixture was overwhelmed with water and extracted with chloroform. The aqueous portion was acidified with excess 1N HCl and extracted with ethyl acetate. The combined organic extracts were washed with brine, dried (sodium sulfate), filtered, and evaporated to give 0.09 g of the titled compound as an off-white crystalline solid: mp 201°–202° C.; MS m/z 314 ($M^+$).

Preparation 4
4A. 7-Methoxybenzo[b]indeno[2,1-d]thiophen-10-one

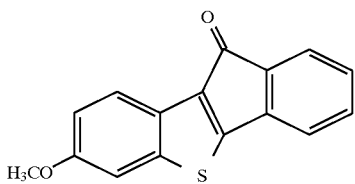

To a slurry of 15.0 g of 6-methoxy-3-carboxylic acid-2-phenylbenzo[b]thiophene and 4 drops of N,N-dimethylformamide in 300 ml of 1,2-dichloroethane at 22° C. was added 15.1 ml of thionyl chloride. The slurry was refluxed for 45 minutes, then evaporated to dryness. The solid was dissolved in 300 ml of dichloromethane and 15.5 g of aluminum chloride was added. The solution was refluxed for 3 hours then poured onto ice and extracted with three portions of chloroform. The chloroform extracts were washed with three portions of brine, dried (sodium sulfate) and evaporated to give 14.1 g of the title compound as a red solid: MS m/z 266 ($M^+$); 300-MHz $^1$H NMR (CDCl$_3$) δ 3.89 (s, 3H), 7.05–7.40 (m, 5H), 7.45 (d, J=7 Hz, 1H), 8.00 (d, J=8 Hz, 1H); Anal. Calcd for $C_{16}H_{10}O_2S$: C, 72.16; H, 3.79. Found: C, 72.00; H, 3.74.

4B. 2,7-Dimethoxybenzo[b]indeno[2,1-d]thiophen-10-one

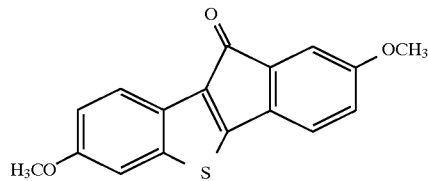

By following the procedure of part A, and substituting 6-methoxy-3-carboxylic acid-2-phenylbenzo[b]thiophene with 6-methoxy-3-carboxylic acid-2-[4-methoxyphenyl]benzo[b]thiophene; the title compound was obtained: MS m/z 296 ($M^+$). Anal. Calcd for $C_{17}H_{12}O_3S$: C, 68.90; H, 4.08; S, 10.82. Found: C, 69.12; H, 4.10; S, 10.68.

Example 3
3A. 10-[4-[2-(1-Piperidinyl)ethoxy]phenyl]-7-methoxy benzo[b]indeno[2,1-d]thiophen-10-ol

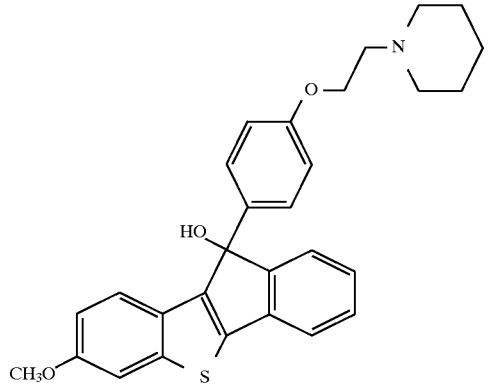

To a solution of 4.2 g of 4-iodo-[2-(1-piperidinyl)ethoxyl]benzene in 400 ml of diethylether at −78° C. was added 16.0 ml of 1.7M t-butyllithium in pentane dropwise. The resulting slurry was cannulated to a solution of 3.0 g of 7-methoxy-benzo[b]indeno[2,1-d]thiophen-10-one in 400 ml of tetra-hydrofuran at −78° C. The solution was stirred for 2 hours at −78° C. then warmed to room temperature and quenched with saturated aqueous sodium bicarbonate. The organics were evaporated off and the resulting aqueous slurry was extracted with three portions of chloroform. The chloroform extracts were washed with three portions of brine, dried (sodium sulfate), filtered and evaporated. The resulting solid was recrystallized from chloroform and hexanes to give 2.5 g of the title compound as a white crystalline solid: MS m/z 471 ($M^+$); 300-MHz $^1$H NMR (CDCl$_3$) δ 1.38–1.50 (m, 2H), 1.50–1.70 (m, 4H), 2.40–2.60 (m, 4H), 2.60–2.80 (m, 3H), 3.86 (s, 3H), 4.00–4.16 (m, 2H), 6.80 (d, J=9 Hz, 2H), 6.90 (d, J=11 Hz, 1H), 7.17 (d, J=7 Hz, 1H), 7.20–7.45 (m, 7H).

3B. 10-[4-[2-(1-Piperidinyl)ethoxy]phenyl]-2,7-dimethoxy benzo[b]indeno[2,1-d]thiophen-10-ol

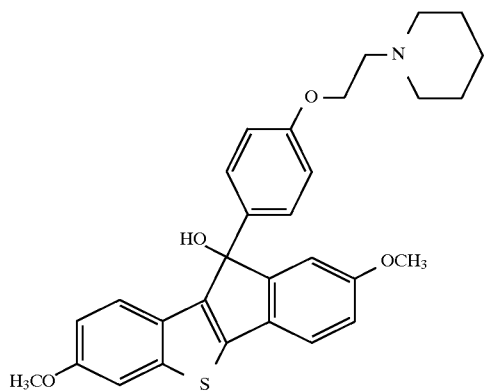

By following the procedure of part A, and substituting 7-methoxy-benzo[b]indeno[2,1-d]thiophen-10-one with 2,7-dimethoxy-benzo[b]indeno[2,1-d]thiophen-10-one; the title compound was obtained: MS m/z 501 ($M^+$); 300-MHz $^1$H NMR (CDCl$_3$) δ 1.35–1.50 (m, 2H), 1.50–1.60 (m, 4H), 2.35–2.55 (m, 4H), 2.60–2.73 (m, 3H), 3.75 (s, 3H), 3.82 (s, 3H), 3.90–4.08 (m, 2H), 6.75–6.80 (m, 2H), 6.80–7.00 (m, 3H), 7.22–7.43 (m, 5H). Anal. Calcd for $C_{30}H_{31}NO_4S$: C, 71.83; H, 6.23; N, 2.79. Found: C, 71.57; H, 6.41; N, 2.75.

Example 4
10-[4-[2-(1-Piperidinyl)ethoxy]phenyl]-7-hydroxy benzo[b]indeno[2,1-d]thiophen-10-ol

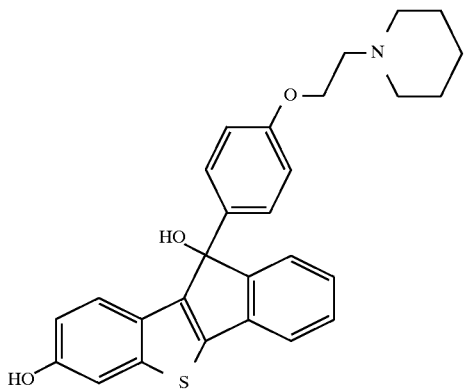

Lithium ethylthiolate was prepared by adding 18.2 ml of 1.6M n-butyllithium in hexanes dropwise to a solution of 2.06 ml of ethanethiol in 125 ml of diethylether at 0° C. The reaction mixture was evaporated to give lithium ethylthiolate as a white crystalline solid. To a solution of lithium ethylthiolate in 150 ml of N,N-dimethylformamide at 22° C. was added 1.29 g of 10-[4-[2-(1-piperidinyl)ethoxy]phenyl]-7-methoxy benzo[b]indeno[2,1-d]thiophen-10-ol. The resulting solution was refluxed for 2 hours, quenched with saturated aqueous sodium bicarbonate and extracted with three portions of chloroform. The chloroform extracts were washed with three portions of water and brine, dried (sodium sulfate), filtered and evaporated. The resulting oil was chromatographed over silica gel eluting with methanol in dichloromethane. The desired product was subsequently purified by cystallization from dichloromethane to give 0.93 g of the title compound as a yellow crystalline solid: MS m/z 457 (M$^+$); 300-MHz $^1$H NMR (DMSO-d$_6$) δ 1.25–1.40 (m, 2H), 1.40–1.50 (m, 4H), 2.25–2.50 (m, 4H), 2.50–2.70 (m, 2H), 3.90–4.00 (m, 2H), 6.25 (s, 1H), 6.70–6.85 (m, 3H), 7.10–7.35 (m, 7H), 7.39 (d, J=7 Hz, 1H), 9.64 (s, 1H); Anal. Calcd for C$_{28}$H$_{27}$NO$_3$S: C, 73.50; H, 5.95; N, 3.06. Found: C, 73.32; H, 5.94; N, 3.21.

Example 5
5A. 10-[4-[2-(1-Piperidinyl)ethoxy]phenyl]-7-methoxy benzo[b]indeno[2,1-d]thiophene

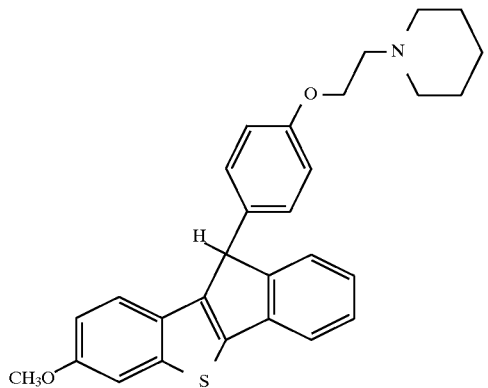

To a solution of 0.14 ml of triethylsilane in 3 ml of trifluoroacetic acid at 0° C. was added a solution of 0.20 g of 10-[4-[2-(1-piperidinyl)ethoxy]phenyl]-7-methoxy benzo[b]indeno [2,1-d]thiophen-10-ol in 10 ml of dichloromethane at 0° C. The reaction solution was stirred for 30 minutes and quenched by the addition of ice. The organic portion was separated from the mixture and washed with three portions of saturated aqueous sodium bicarbonate and brine, dried (sodium sulfate), filtered and evaporated to dryness. The resulting brown oil was chromatographed over silica gel eluting with methanol in dichloromethane to provide 160 mg of the title compound as a yellow solid: MS m/z 456 (M$^+$); 300-MHz $^1$H NMR (CDCl$_3$) δ 1.40–1.50 (m, 2H), 1.50–1.65 (m, 4H), 2.42–2.58 (m, 4H), 2.74 (t, J=6 Hz, 2H), 3.85 (s, 3H), 4.06 (t, J=6 Hz, 2H), 4.96 (s, 1H), 6.83 (d, J=8 Hz, 2H), 6.85 (d, J=8 Hz, 1H), 7.05 (d, J=8 Hz, 2H), 7.17 (d, J=8 Hz, 1H), 7.23–7.40 (m, 4H), 7.48 (d, J=8 Hz, 1H). Anal. Calcd for C$_{29}$H$_{29}$NO$_2$S: C, 76.45; H, 6.42; N, 3.07. Found: C, 76.22; H, 6.45; N, 3.03.

5B. 10-[4-[2-(1-Piperidinyl)ethoxy]phenyl]-2,7-dimethoxybenzo[b]indeno[2,1-d]thiophene

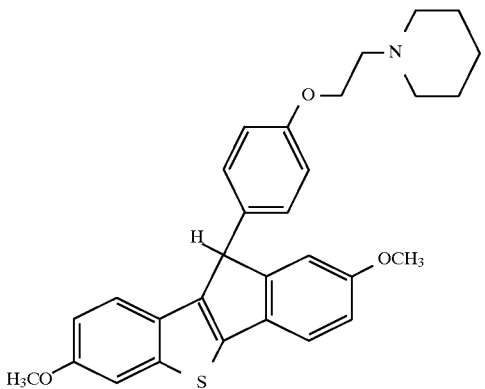

By following the procedure of part A, and substituting 10-[4-[2-(1-piperidinyl)ethoxy]phenyl]-7-methoxybenzo[b]indeno [2,1-d]thiophen-10-ol with 10-[4-[2-(1-piperidinyl)ethoxy]phenyl]-2,7-dimethoxybenzo[b]indeno[2,1-d]thiophen-10-ol; the title compound was obtained: MS m/z 485 (M$^+$); 300-MHz $^1$H NMR (CDCl$_3$) δ 1.40–1.50 (m, 2H), 1.50–1.70 (m, 4H), 2.42–2.60 (m, 4H), 2.72–2.84 (m, 2H), 3.79 (s, 3H), 3.86 (s, 3H), 4.00–4.20 (m, 2H), 4.93 (s, 1H), 6.80–7.00 (m, 5H), 7.06 (d, J=9 Hz, 1H), 7.20–7.40 (m, 4H). Anal. Calcd for C$_{30}$H$_{31}$NO$_3$S: C, 74.20; H, 6.43; N, 2.88. Found: C, 73.92; H, 6.50; N 2.78.

Example 6
10-[4-[2-(1-Piperidinyl)ethoxy]phenyl]-7-hydroxy benzo[b]indeno[2,1-d]thiophene hydrochloride

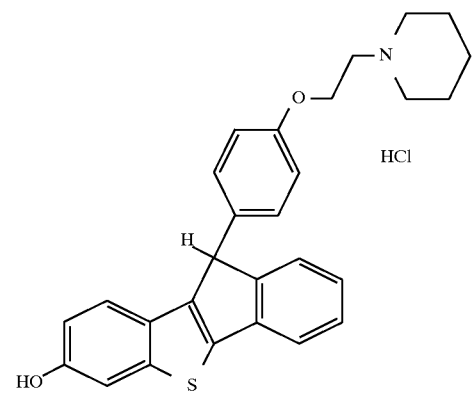

To a solution of 0.55 g of 10-[4-[2-(1-piperidinyl)ethoxy]phenyl]-7-methoxy benzo[b]indeno [2,1-d]thiophene in 25 ml of dichloromethane was added 0.44 ml of ethanethiol followed by 0.8 g of aluminum chloride. The resulting solution was stirred 1 hour at 22° C. and quenched with saturated aqueous sodium bicarbonate. The mixture was exhaustively extracted with dichloroethane. The combined organic extracts were washed with three portions of brine, dried (sodium sulfate), filtered and evaporated to dryness. The resulting solid was dissolved in 30 ml of methanol and 1.45 ml of 1N hydrochloric acid was added, then evaporated to dryness. The resulting solid was recrystallized from ethanol and ether to give 310 mg of the title compound as a white crystalline solid: MS m/z 441 (M$^+$); 300-MHz $^1$H NMR (DMSO) δ 1.60–1.80 (m, 6H), 2.90–3.10 (m, 2H), 3.35–3.50 (m, 4H), 4.25–4.35 (m, 2H), 5.16 (s, 1H), 6.76 (d, J=9 Hz, 1H), 6.90 (d, J=9 Hz, 2H), 7.06 (d, J=9 Hz, 2H), 7.10–7.25 (m, 3H), 7.25–7.35 (m, 2H), 7.52 (d, J=7 Hz, 1H), 9.70 (s, 1H), 10.00 (br s, 1H). Anal. Calcd for $C_{28}H_{28}NO_2SCl$: C, 70.35; H, 5.90; N, 2.93. Found: C, 70.13; H, 6.09; N, 2.98.

Test Procedures

In the examples illustrating the methods, a postmenopausal model was used in which effects of different treatments upon circulating lipids were determined.

Seventy-five day old female Sprague Dawley rats (weight range of 200 to 225 g) were obtained from Charles River Laboratories (Portage, Mich.). The animals were either bilaterally ovariectomized (OVX) or exposed to a Sham surgical procedure at Charles River Laboratories, and then shipped after one week. Upon arrival, they were housed in metal hanging cages in groups of 3 or 4 per cage and had ad libitum access to food (calcium content approximately 0.5%) and water for one week. Room temperature was maintained at 22.2°±1.7° C. with a minimum relative humidity of 40%. The photoperiod in the room was 12 hours light and 12 hours dark.

Dosing Regimen Tissue Collection. After a one week acclimation period (therefore, two weeks post-OVX) daily dosing with test compound was initiated. 17α-ethynyl estradiol or the test compound were given orally, unless otherwise stated, as a suspension in 1% carboxymethylcellulose or dissolved in 20% cyclodextrin. Animals were dosed daily for 4 days. Following the dosing regimen, animals were weighed and anesthetized with a ketamine: xylazine (2:1, V:V) mixture and a blood sample was collected by cardiac puncture. The animals were then sacrificed by asphyxiation with $CO_2$, the uterus was removed through a midline incision, and a wet uterine weight was determined.

Cholesterol Analysis. Blood samples were allowed to clot at room temperature for 2 hours, and serum was obtained following centrifugation for 10 minutes at 3000 rpm. Serum cholesterol was determined using a Boehringer Mannheim Diagnostics high performance cholesterol assay. Briefly the cholesterol was oxidized to cholest-4-en-3-one and hydrogen peroxide. The hydrogen peroxide was then reacted with phenol and 4-aminophenazone in the presence of peroxidase to produce a p-quinone imine dye, which was read spectrophotemetrically at 500 nm. Cholesterol concentration was then calculated against a standard curve.

Uterine Eosinophil Peroxidase (EPO) Assay. Uteri were kept at 4° C. until time of enzymatic analysis. The uteri were then homogenized in 50 volumes of 50 mM Tris buffer (pH-8.0) containing 0.005% Triton X-100. Upon addition of 0.01% hydrogen peroxide and 10 mM O-phenylenediamine (final concentrations) in Tris buffer, increase in absorbance was monitored for one minute at 450 nm. The presence of eosonophils in the uterus is an indication of estrogenic activity of a compound. The maximal velocity of a 15 second interval was determined over the initial, linear portion of the reaction curve.

Source of Compound: 17α-ethynyl estradiol was obtained from Sigma Chemical Co., St. Louis, Mo.

Influence of Formula I Compounds on Serum Cholesterol and Determination of Agonist/Non-Agonist Activity Data presented in Table 1 below show comparative results among ovariectomized rats, rats treated with 17α-ethynyl estradiol ($EE_2$; an orally available form of estrogen), and rats treated with certain compounds of the instant invention. Although $EE_2$ caused a decrease in serum cholesterol when orally administered at 0.1 mg/kg/day, it also exerted a stimulatory action on the uterus so that $EE_2$ uterine weight was substantially greater than the uterine weight of ovariectomized test animals. This uterine response to estrogen is well recognized in the art.

Not only did the compounds of the instant invention generally reduce serum cholesterol compared to the ovariectomized control animals, but uterine weight was only minimally increased to slightly decreased with the majority of the formula compounds tested. Compared to estrogenic compounds known in the art, the benefit of serum cholesterol reduction without adversely affecting uterine weight is quite rare and desirable.

As is expressed in the data below, estrogenicity also was assessed by evaluating the adverse response of eosinophil infiltration into the uterus. The compounds of the instant invention did not cause any increase in the number of eosinophils observed in the stromal layer of ovariectomized rats, while estradiol cause a substantial, expected increase in eosinophil infiltration.

The data presented in Table 1 below reflects the response of 5 to 6 rats per treatment.

TABLE 1

| Compound | Dose mg/kg[a] | Uterine Weight % Increase[b] | Uterine Eosinophil (Vmax)[c] | Serum Cholest. % Decrease[d] |
|---|---|---|---|---|
| $EE_2$e | 0.1 | 169.5* | 144.0* | 90.5* |
| Example 9 | 0.1 | 17.3 | 4.6 | 15.2 |
|  | 1 | 5.57* | 34.6 | 52.5* |
|  | 10 | 87.1* | 87.4* | 64.4* |
| Example 6 | 0.1 | 32.5* | 2.9 | 1.3 |
|  | 1 | 67.4* | 3.7 | 40.6* |
|  | 10 | 54.0* | 29.8* | 69.9* |
| Example 5A | 0.1 | 33.8* | 6.4 | 59.1* |
|  | 1 | 63.5* | 35.4* | 74.4* |
|  | 10 | 92.9* | 31.8* | 60.3* |
| Example 1B | 0.1 | 21 | 4.8 | 56.8* |
|  | 1 | 31.8* | 34.2 | 71.0* |
|  | 10 | 27.7* | 50.4* | 75.3* |
| Example 3B | 0.1 | 50.4* | 36.0* | 43.5* |
|  | 1 | 43.0* | 36.6* | 62.5* |
|  | 10 | 28.2* | 19.2 | 69.2 |
| Example 1A | 0.1 | 19.2 | 7.2 | 59.1* |
|  | 1 | 21.6 | 30.3 | 47.7* |
|  | 10 | 26.8 | 21.9 | 68.7* |
| Example 2 | 0.1 | 14.6 | 4.8 | 41.4* |
|  | 1 | 25.6 | 24.0 | 52.5* |
|  | 10 | 18.3 | 23.4 | 66.3* |

[a]g/kg PO
[b]Uterine weight % increase verses ovariectomized controls
[c]Eosinophil peroxidase, Vmax
[d]Serum cholesterol decrease verses ovariectomized controls
[e]17-α-Ethynyl estradiol
*p < 0.05

In addition to the demonstrated benefits of the compounds of the instant invention, the above data clearly demonstrate that compounds of Formula I are not estrogen mimetics. Furthermore, no deleterious toxicological effects (for example, survival numbers) were observed with any treatment.

Osteoporosis Test Procedure

Following the General Preparation Procedure, infra, the rats are treated daily for 35 days (6 rats per treatment group) and sacrificed by carbon dioxide asphyxiation on the 36th day. The 35 day time period is sufficient to allow maximal reduction in bone density, measured as described herein. At the time of sacrifice, the uteri are removed, dissected free of extraneous tissue, and the fluid contents are expelled before determination of wet weight in order to confirm estrogen deficiency associated with complete ovariectomy. Uterine weight is routinely reduced about 75% in response to ovariectomy. The uteri are then placed in 10% neutral buffered formalin to allow for subsequent histological analysis.

The right femurs are excised and digitilized x-rays generated and analyzed by an image analysis program (NIH image) at the distal metaphysis. The proximal aspect of the tibiae from these animals are also scanned by quantitative computed tomography.

In accordance with the above procedures, compounds of the instant invention and ethynyl estradiol ($EE_2$) in 20% hydroxypropyl β-cyclodextrin are orally administered to test animals. Distal femur metaphysis and proximal tibiae data are the results of formula I compound treatments compared to intact and ovariectomized test animals. Results are reported as percent protection relative to ovariectomy in Table 2 below.

TABLE 2

|  | Dose mg/kg | Femur. % Protection (x-ray image) | Femur BMD % protection |
|---|---|---|---|
| EE2 | 0.1 | 99.1 | 76.3 |
| Example 6 | 0.01 | 53.8 | 40.4 |
|  | 0.1 | 39.2 | 46.6 |
|  | 1 | 73.4 | 66.6 |
|  | 10 | 48.2 | 64.0 |

In summary, ovariectomy of the test animals causes a significant reduction in femur density compared to intact, vehicle treated controls. Orally administered ethynyl estradiol ($EE_2$) prevents this loss, but the risk of uterine stimulation with this treatment is ever-present.

The compounds of the instant invention also prevented bone loss in a general, dose-dependent manner. Accordingly, the compounds of the instant invention are useful for the treatment of osteoporosis, particularly caused by postmenopausal syndrome.

MCF-7 Proliferation Assay

MCF-7 breast adenocarcinoma cells (ATCC HTB 22) were maintained in MEM (minimal essential medium, phenol red-free, Sigma, St. Louis, Mo.) supplimented with 10% fetal bovine serum (FBS) (V/V), L-glutamine (2 mM), sodium pyruvate (1 mM), HEPES {(N-[2-hydroxyethyl] piperazine-N'-[2-ethanesulfonic acid]10 mM}, non-essential amino acids and bovine insulin (1 μg/mL) (maintenance medium). Ten days prior to assay, MCF-7 cells were switched to maintenance medium supplemented with 10% dextran coated charcoal stripped fetal bovine serum (DCC-FBS) assay medium) in place of 10% FBS to deplete internal stores of steroids. MCF-7 cells were removed from maintenance flasks using cell dissociation medium ($Ca^{++}/Mg^{++}$ free HBSS (phenol red-free) supplemented with 10 mM HEPES and 2 mM EDTA). Cells were washed twice with assay medium and adjusted to 80,000 cells/mL. Approximately 100 mL (8,000 cells) were added to flat-bottom microculture wells (Costar 3596) and incubated at 37° C. in a 5% $CO_2$ humidified incubator for 48 hours to allow for cell adherence and equilibration after transfer. Serial dilutions of drugs or DMSO as a diluent control were prepared in assay medium and 50 mL transferred to triplicate microcultures followed by 50 mL assay medium for a final volume of 200 mL. After an additional 48 hours at 37° C. in a 5% $CO_2$ humidified incubator, microcultures were pulsed with tritiated thymidine (1 uCi/well) for 4 hours. Cultures were terminated by freezing at −70° C. for 24 hours followed by thawing and harvesting of microcultures using a Skatron Semiautomatic Cell Harvester. Samples were counted by liquid scintillation using a Wallace BetaPlace β counter. Results in Table 3 below show the $ED_{50}$ (nM) for certain compounds of the instant invention:

TABLE 3

| Compound | $ED_{50}$ (nM) |
|---|---|
| Example 1A | 200 |
| Example 1B | 100 |
| Example 2 | 0.10 |
| Example 6 | 10 |

DMBA-Induced Mammary Tumor Inhibition

Estrogen-dependent mammary tumors are produced in female Sprague-Dawley rats which are purchased from Harlan Industries, Indianapolis, Ind. At about 55 days of age, the rats receive a single oral feeding of 20 mg of 7,12-dimethylbenzo[a]anthracene (DMBA). About 6 weeks after DMBA administration, the mammary glands are palpated at weekly intervals for the appearance of tumors. Whenever one or more tumors appear, the longest and shortest diameters of each tumor are measured with a metric caliper, the measurements are recorded, and that animal is selected for experimentation. An attempt is made to uniformly distribute the various sizes of tumors in the treated and control groups such that average-sized tumors are equivalently distributed between test groups. Control groups and test groups for each experiment contain 5 to 9 animals.

Compounds of Formula I are administered either through intraperitoneal injections in 2% acacia, or orally. Orally administered compounds are either dissolved or suspended in 0.2 mL corn oil. Each treatment, including acacia and corn oil control treatments, is administered once daily to each test animal. Following the initial tumor measurement and selection of test animals, tumors are measured each week by the above-mentioned method. The treatment and measurements of animals continue for 3 to 5 weeks at which time the final areas of the tumors are determined. For each compound and control treatment, the change in the mean tumor area is determined.

We claim:
1. A compound of formula I:

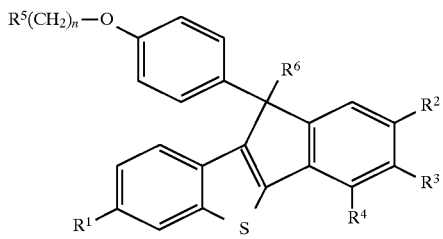

wherein:
R¹ is —H, —OH, —X, where —X is a halogen, —O($C_1$–$C_4$ alkyl), —OCO($C_1$–$C_6$ alkyl), —OCO(O) ($C_1$–$C_6$ alkyl), —OCOAr, —OCO(O)Ar where Ar is phenyl or substituted phenyl, or —OSO$_2$($C_4$–$C_6$ alkyl);

R², R³, and R⁴ are independently —H, —OH, —X, where —X is a halogen, —O($C_1$–$C_4$ alkyl), —OCO($C_1$–$C_6$ alkyl), —OCO(O) ($C_1$–$C_6$ alkyl), —OCOAr, —OCO(O)Ar where Ar is phenyl or substituted phenyl, or —OSO$_2$ ($C_4$–$C_6$ alkyl);

n is 2 or 3;

R⁵ is 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino; and R⁶ is —H, —OH, —X, where —X is a halogen, —CN, —NH$_2$, —NHR⁸, —NR⁸R⁹, where R⁸ and R⁹ are both independently $C_1$–$C_6$ alkyl, or $C_1$–$C_6$ alkyl; or a pharmaceutically acceptable salt or solvate thereof.

2. A compound according to claim 1 wherein n is two.

3. A compound according to claim 1 wherein R¹ is methoxy.

4. A compound according to claim 1 wherein R² is methoxy.

5. A compound according to claim 1 wherein R¹ is hydroxy.

6. A compound according to claim 1 wherein R² is hydroxy.

7. A compound according to claim 1 wherein R³ is hydrogen.

8. A compound according to claim 1 wherein R⁵ is 1-piperidinyl.

9. A compound according to claim 1 wherein R² and R⁴ are both hydrogen.

10. A compound according to claim 1 selected from the group consisting of
10-[4-[2-(1-Piperidinyl)ethoxy]phenyl]-3,7-dimethoxy benzo[b]indeno[2,1-d]thiophene;
10-[4-[2-(1-Piperidinyl)ethoxy]phenyl]benzo[b]indeno[2,1-d]thiophene;
10-[4-[2-(1-Piperidinyl)ethoxy]phenyl]-3,7-dihydroxy benzo[b]indeno[2,1-d]thiophene;
10-[4-[2-(1-Piperidinyl)ethoxy]phenyl]-7-methoxy benzo[b]indeno[2,1-d]thiophen-10-ol;
10-[4-[2-(1-Piperidinyl)ethoxy]phenyl]-2,7-dimethoxy benzo[b]indeno[2,1-d]thiophen-10-ol;
10-[4-[2-(1-Piperidinyl)ethoxy]phenyl]-7-hydroxy benzo[b]indeno[2,1-d]thiophen-10-ol;
10-[4-[2-(1-Piperidinyl)ethoxy]phenyl]-7-methoxy benzo[b]indeno[2,1-d]thiophene;
10-[4-[2-(1-Piperidinyl)ethoxy]phenyl]-2,7-dimethoxybenzo[b]indeno[2,1-d]thiophene;
10-[4-[2-(1-Piperidinyl)ethoxy]phenyl]-7-hydroxy benzo[b]indeno[2,1-d]thiophene hydrochloride;
10-[4-[2-(1-Pyrrolidinyl)ethoxy]phenyl]-3,7-dimethoxy benzo[b]indeno[2,1-d]thiophene;
10-[4-[2-(1-Pyrrolidinyl)ethoxy]phenyl]benzo[b]indeno[2,1-d]thiophene;
10-[4-[2-(1-Pyrrolidinyl)ethoxy]phenyl]-3,7-dihydroxy benzo[b]indeno[2,1-d]thiophene;
10-[4-[2-(1-Pyrrolidinyl)ethoxy]phenyl]-7-methoxy benzo[b]indeno[2,1-d]thiophen-10-ol;
10-[4-[2-(1-Pyrrolidinyl)ethoxy]phenyl]-2,7-dimethoxy benzo[b]indeno[2,1-d]thiophen-10-ol;
10-[4-[2-(1-Pyrrolidinyl)ethoxy]phenyl]-7-hydroxy benzo[b]indeno[2,1-d]thiophen-10-ol;
10-[4-[2-(1-Pyrrolidinyl)ethoxy]phenyl]-7-methoxy benzo[b]indeno[2,1-d]thiophene;
10-[4-[2-(1-Pyrrolidinyl)ethoxy]phenyl]-2,7-dimethoxybenzo[b]indeno[2,1-d]thiophene; and
10-[4-[2-(1-Pyrrolidinyl)ethoxy]phenyl]-7-hydroxy benzo[b]indeno[2,1-d]thiophene hydrochloride.

11. A method of inhibiting bone loss or bone resorption which comprises administering to a patient in need thereof an effective amount of a compound of claim 1.

12. A method according to claim 11, wherein said bone loss or bone resorption is due to menopause or ovariectomy.

13. A method of lowering serum cholesterol levels which comprises administering to a patient in need thereof an effective amount of a compound of claim 1.

14. A method of inhibiting estrogen-dependent cancer which comprises administering to a patient in need thereof an effective amount of a compound of claim 1.

15. A method according to claim 14 wherein said estrogen-dependent cancer is breast cancer.

16. A method according to claim 14 wherein said estrogen-dependent cancer is uterine cancer.

* * * * *